United States Patent [19]

Cooley

[11] 4,164,046

[45] Aug. 14, 1979

[54] VALVE PROSTHESIS

[76] Inventor: Denton A. Cooley, 3014 Del Monte, Houston, Tex. 77019

[21] Appl. No.: 797,107

[22] Filed: May 16, 1977

[51] Int. Cl.² .............................................. A61F 1/22
[52] U.S. Cl. ........................................................ 3/1.5
[58] Field of Search ................................. 3/1.5, 1.4, 1

[56] References Cited

U.S. PATENT DOCUMENTS

| | | | |
|---|---|---|---|
| 3,508,281 | 4/1970 | Cromie | 3/1.5 |
| 3,534,411 | 10/1970 | Shiley | 3/1.5 |
| 3,656,185 | 4/1972 | Carpentier | 3/1.5 |
| 3,714,671 | 2/1973 | Edwards et al. | 3/1.5 |
| 4,042,979 | 8/1977 | Angell | 3/1.5 |
| 4,055,861 | 11/1977 | Carpentier et al. | 3/1.5 |

FOREIGN PATENT DOCUMENTS 2461370  7/1975  Fed. Rep. of Germany ............... 3/1.4

*Primary Examiner*—Ronald L. Frinks
*Attorney, Agent, or Firm*—H. Ross Workman; J. Winslow Young

[57] ABSTRACT

An improved valve prosthesis for mitral and tricuspid heart valves, the valve prosthesis being configured as an open ring and covered with a double velour fabric having a laterally projecting fabric appendage for simultaneously facilitating suturing the prosthesis in place and improving tissue infiltration.

3 Claims, 10 Drawing Figures

VALVE PROSTHESIS

BACKGROUND

1. Field of the Invention

The present invention relates to an improved heart valve prosthesis for use in improving the function of the mitral and/or tricuspid heart valves.

2. The Prior Art

The bicuspid or mitral valve is located in the left atrioventricular opening of the heart. It is encircled by a dense fibrous ring and consists of two valve leaflets of unequal size. The larger valve leaflet (called ventral or anterior cusp) is placed adjacent the aortic opening. The smaller leaflet is the dorsal or posterior cusp. The leaflets are composed of strong fibrous tissue which is thick in the central part but thin and translucent near the margin. The valves are constructed so as to pass blood unidirectionally from the left atrium to the left ventricle of the heart.

The tricuspid valve is located in the right atrioventricular opening and comprises three leaflets sometimes referred to as the anterior, posterior and septal cusps. The leaflets are roughly triangular in shape and attached to a fibrous ring with the apices projecting into the ventricular cavity.

Both the mitral and tricuspid valves are intended to prevent regurgitation of blood from the ventricle into the atrium when the ventricle contracts. In order to withstand the substantial back pressure and prevent regurgitation of blood into the atrium during the ventricular contraction, the cusps are held in place by delicate but strong fibrous cords which anchor the valve cusps to the muscular wall of the heart.

In some well recognized instances of heart disease, however, valve leaflet prolapse is evident. Prolapse of the valve leaflet appears to result from a dilatation or elongation of the posterior two-thirds of the valve annulus. A number of circumstances may cause the valve defect. The result of the defect, however, is the failure of normal apposition of the leaflets. When the leaflets fail to close completely during ventricular systole, the leaflets become damaged, the cords ruptured and the atrioventricular annulus distended. The result of the valve prolapse is a syndrome often associated with chest pain, cardiac arrythmias, dyspnea, and other adverse clinical symptoms.

One obvious solution to a serious valve prolapse is total valve replacement. It is generally agreed, however, that total valve replacement is too radical except in the most advanced cases. Accordingly, treatment of valve prolapse by techniques of annuloplasty have become more commonplace.

One of the more common annuloplastic techniques is schematically illustrated in FIG. 1 of the drawing and consists of suturing (plicating) the two valve leaflets together at the commissures so as to reduce the size of the opening through which blood can pass. The purpose of this suture is to draw the anterior and posterior cusps sufficiently close together that normal apposition will occur during ventricular systole. Experience has proved, however, that plication of the annulus at the commissures places extreme stress on the tissue adjacent the sutures with the unfortunate result that the sutures tear from the tissue damaging the leaflets and recreating the conditions susceptible to prolapse.

A valve prosthesis for mitigating the serious valve insufficiency described above is suggested by Carpentier in the Journal of Thoracic and Cardiovascular Surgery Volume 61, No. 1, January 1971. The prior art valve prosthesis described therein consists of a rigid circular or oval ring covered with a Teflon fabric which permits the ring to be sutured in place. The Carpentier ring was an improvement in many respects over earlier techniques. However, two inherent disadvantages in the Carpentier ring have become apparent. First, in order to secure the ring in place, suture placement is required along the anterior section of the annulus adjacent the aortic valve. Not infrequently, sutures are inadvertently passed into the aortic valve so as to interfere with the valve function. Moreover, to secure the rigid structure adjacent the largest (anterior) leaflet has the effect of interfering with mitral valve function. Second, with the passage of time sutures used for securing prior art prostheses may be subject to degeneration as a result of continual heart and valve action. Suture degeneration can result in separation of the prosthesis from its secured position causing at least partial failure of the prosthesis and risking interference with valve function.

Accordingly, it would be a significant improvement in the art to provide a heart valve prosthesis which restores valve function without interfering with adjacent valves and which would promote tissue adherence through natural fibroblastic growth and endothelization through natural processes so as to maintain the prosthesis securely in place. Such an improvement is disclosed and claimed herein.

BRIEF SUMMARY AND OBJECTS OF THE INVENTION

The present invention comprises a uniquely shaped open ring valve prosthesis having a special velour exterior for effecting mitral and tricuspid annuloplasty and for overcoming valve incompetence. The surface of the valve promotes a surprising degree of tissue infiltration and adherence.

It is, therefore, a primary object of the present invention to provide an improved heart valve prosthesis.

It is another valuable object of the present invention to provide a valve prosthesis for the mitral and tricuspid valves which are configurated in the form of an open ring.

Another important object of the present invention is to provide a heart valve prosthesis having an exterior coating of velour fabric.

Another object of the present invention is to provide an open ring mitral valve prosthesis constructed to leave at least the anterior valve completely without rigid support while at the same time contracting the valve annulus in the vicinity of the posterior leaflet and valve commissures.

Another object of the present invention is to provide a tricuspid valve prosthesis configurated as an open ring, the open portion of the ring being constructed to leave most of the posterior leaflet mobile while securing the tricuspid valve annulus.

These and other objects and features of the present invention will become more fully apparent from the following description and appended claims taken in conjunction with the accompanying drawing.

DETAILED DESCRIPTION OF THE PREFERRED EMBODIMENTS

The present invention, as represented by the presently preferred embodiments disclosed herein, provide a valve collar prosthesis which restores valve competence and at the same time promotes a surprising degree of fibroblastic growth and endotheliazation to assure that the prosthesis will remain in place and continue its function even if the sutures should degenerate over time.

Figure 1:
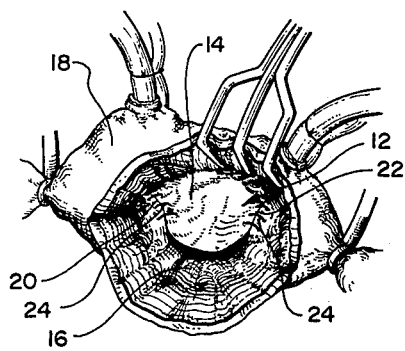
FIG. 1 is a schematic illustration of the prior art technique of effecting annuloplasty through plication of annulus at the commissures.

Referring now to FIG. 1, a schematic illustration of one widely recognized prior art technique for valve annuloplasty is illustrated. In FIG. 1, a mitral valve generally designated 12 is illustrated. The mitral valve has an anterior leaflet 14 and a smaller posterior leaflet 16. For convenience, the left atrium 18 is illustrated schematically.

At the commissures 20 and 22, the leaflets 14 and 16 are secured together with sutures 24 for the purpose of reducing the enlarged opening between the leaflets 14 and 16. It is the stretched and enlarged opening between the leaflets which permits prolapse of the valve under pressure from the blood. Unfortunately, however, the sutures 24 tend to tear from the delicate tissue forming the leaflets 14 and 16 under the significant back pressure exerted by the blood.

Figures 2, 3:
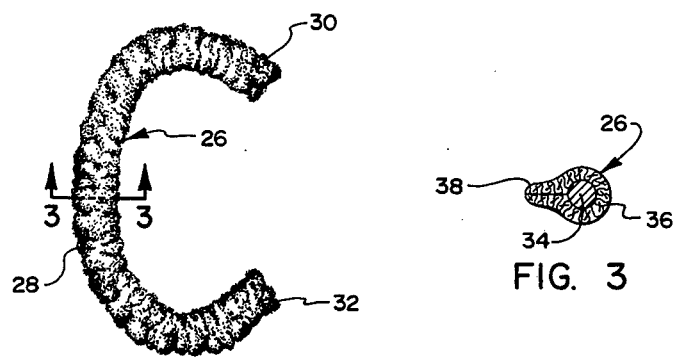
FIG. 2 is a presently preferred mitral valve prosthesis embodiment.
FIG. 3 is a cross section taken along lines 3—3 of FIG. 2.

In accordance with the present invention, one preferred embodiment of which is illustrated in FIG. 2, an open ring valve prosthesis generally designated 26 can be used to effect annuloplasty of a distended mitral valve. Referring now more particularly to FIG. 2, it will be observed that the valve prosthesis is shaped as an open ring having an elongated central member 28 and integral, coplanar ends 30 and 32 which are bent each toward the other. As shown best in FIG. 3, the prosthesis 26 preferably includes a spine comprising comparatively stiff interior rod 34, preferably formed of metal such as titanium. Clearly, other suitable stiff or semirigid materials could be used to form rod 34. The exterior of the rod 34 is encapsulated in a sheath 36 of double velour fabric. The term "double velour" fabric, as used herein means fabric having a velour nap on both front and back surfaces. The ends of the double velour fabric are joined together and project laterally away from the rod 34 to form an appendage 38 of fabric. While any suitable velour fabric could be used, a double velour knitted material formed of Dacron polyester has been found highly effective.

The velour fabric has two significant advantages. First, it provides a convenient medium through which suture can be placed to secure the prosthesis 26 to the surrounding fibrous tissue. Second, the velour fabric has been found surprisingly effective in encouraging endotheliazation. In order to adequately fill the desirable criteria for a valve prosthesis, the encapsulating fabric should be strong, durable and biocompatible and at the same time permit long term healing and incorporation into sorrounding tissues. The "velour" construction has tiny loops of polyester fabric presenting a soft surface with high pile and more pliable consistency which facilitates passage of the suture. Notably, the velour surface of the fabric is present entirely around the rod 34 to permit tissue infiltration from any direction. It was determined that the double velour fabric exhibited surprising resistance to separation from the infiltrated tissue (adventitia). These surprising results were evidenced in part by laboratory investigations comparing double velour, warp knitted fabric and woven Dacron fabric of the low porosity type (see FIG. 8).

In conducting the investigations, anesthetized dogs were intubated endotracheally for respiratory support and the abdominal aorta was exposed by a midline laparotomy. The aorta from just below the renal arteries to the trifurcation was removed and replaced by grafts of the double velour, knitted and woven types. Anastomoses were made with 5-0 polypropylene continuous sutures. The peritoneum was closed over the graft and the abdominal incision was repaired. Intramuscular streptomycin was given for prophylaxis against infection. The dogs were well attended, fed and exercised during the ensuing six weeks and then sacrificed.

Figure 8:
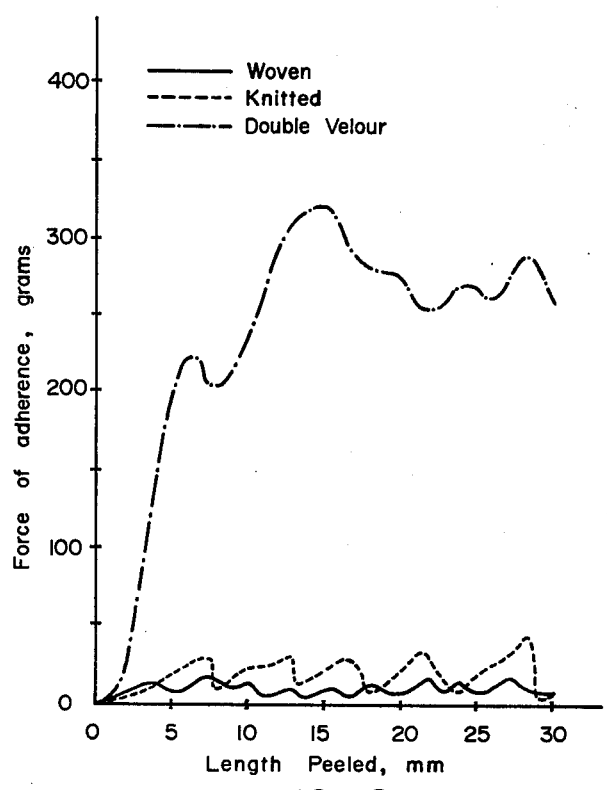
FIG. 8 is a graphical illustration of the surprisingly improved tissue adhesion effected through the use of the double velour fabric utilized by the prosthesis embodiments of this invention.

The grafts were opened longitudinally and examined. Peel tests were performed using a modified Instron tensile strength testing device to ascertain the degree of adherence of the three graft types to the surrounding external tissue. The results of the investigation are illustrated in FIG. 8. The double velour fabric proved to be strikingly more adherent to the surrounding tissue demonstrating more than ten times the force of adherence of the non-double velour fabrics. It is believed that the profound adherence of the double velour grafts to surrounding tissue is the result of rapid fibrous tissue infiltration.

Insertion of the mitral valve prosthesis, as will be understood by persons skilled in the art, is performed by using a standard midline sternotomy. Temporary cardiopulmonary bypass with hemodilution is employed and the mitral valve is exposed through an incision medial to the right pulmonary veins. The distance between the peripheral extent of the commissures or the actual width of the anterior leaflet is measured or estimated and a prosthesis 26 of appropriate size is selected. Typical adequate sizes for the prosthesis 26 would include 25, 30, and 35 millimeters maximum diameter.

The prosthesis 26 is positioned such that the anterior leaflet 12 of the mitral valve is situated in the free zone between the ends 30 and 32 of the prosthesis 26. As shown best in FIG. 6, mattress sutures are symmetrically placed around the prosthesis 26 and through the fabric 36 to maintain proper spacing. A double-needle suture of braided 2-0 polyester is used with a Teflon felt pledget 40 attached individually to the ends of the suture 42.

Figure 7:
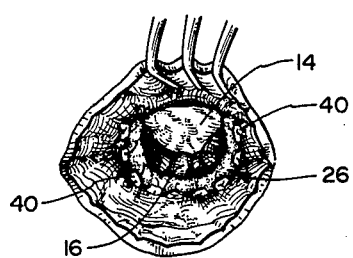
FIG. 7 is a schematic illustration of the mitral valve embodiment of FIG. 2 sutured in place upon a mitral valve.

Use of alternating colored sutures facilitates identification and separation of the suture for tying. The sutures are placed carefully into the fibrous portion 44 of the annulus but not deeply enough to encircle or injure the underlying circumflex branch of the left coronary artery or the coronary sinus. When all of the sutures are tied, the distended annulus is constricted to its normal size and the mitral valve has renewed competence with free action of the anterior leaflet 14. FIG. 7 illustrates the prosthesis in its fully implanted position.

Figure 4:
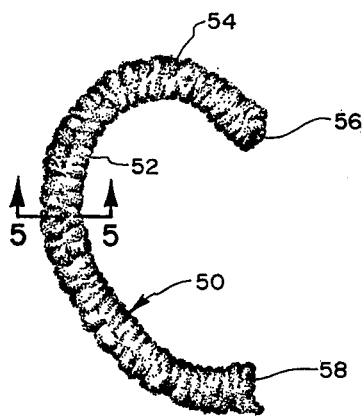
FIG. 4 is a schematic illustration of a presently preferred tricuspid valve prosthesis.
Figure 5:
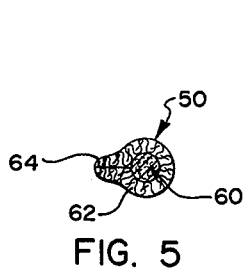
FIG. 5 is a cross section taken along lines 5—5 of FIG. 4.

Another valve prosthesis embodiment generally designated 50 is illustrated in FIGS. 4 and 5. This collar ring prosthesis 50 has a configuration which differs from the configuration of the embodiment of FIG. 2 primarily to accommodate annuloplasty of a tricuspid valve. The prosthesis 50 has an enlarged coplanar ascending portion 52 which turns inwardly at 54 and terminates at end 56. The opposite end 58 traverses a slight bend which, by contrast to the embodiment of FIG. 2, is significantly less than the angle traversed by the end 56. The prosthesis 50, as shown in FIG. 5, has a spine comprising an interior rod 60 which is circumscribed by a velour fabric 62. The rod 60 is preferably formed of titanium metal, however, any suitable biocompatible stiff or semirigid material could be used. The ends of the fabric are joined together to form an appendage 64. Thus, the entire exterior surface of the prosthesis 50 is covered with velour fabric. Preferably the velour fabric is a double velour having nap on both sides thereof.

Figure 6:
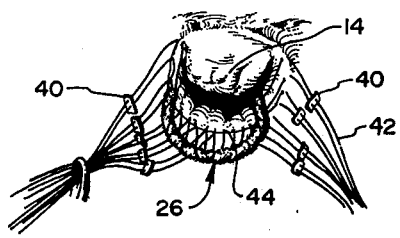
FIG. 6 is an illustration of the mode of implantation of the mitral valve embodiment of FIG. 2.

The tricuspid prosthesis 50 is secured in essentially the same manner as that described in connection with FIG. 6. In the prosthesis 50, however, the ends 56 and 58 are positioned on either side of the posterior or septal leaflet such that the septal leaflet is situated in the free zone between ends 56 and 58 of prosthesis 50. As with the mitral valve prosthesis 26, the prosthesis 50 does not interfere with leaflet function.

Figure 9:
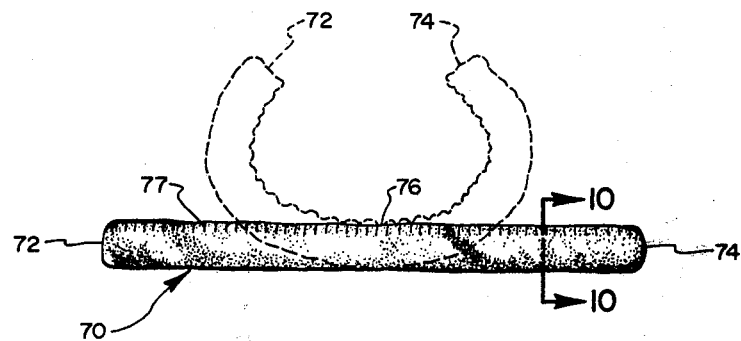
FIG. 9 is a schematic plan view of a flexible valve prosthesis embodiment, the broken line portion representing the configuration into which the prosthesis will be bent upon securement to the mitral valve annulus.
Figure 10:
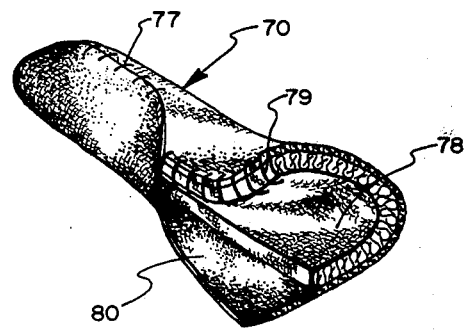
FIG. 10 is a schematic cross-sectional view of the embodiment of FIG. 9 in a state of partial disassembly to reveal interior construction.

Referring to FIGS. 9 and 10, still another presently preferred heart valve prosthesis generally designated 70 is illustrated. The prosthesis 70 differs from the embodiments illustrated in FIGS. 2 and 4 primarily in that the prosthesis has a more flexible construction. With particular reference to FIG. 10, the prosthesis 70 is interiorly provided with a flexible interior spine 78 preferably formed of braided dactron tape. The flexible spine 78 is sutured at 79 to a second velour fabric 80. Preferably, the fabric 80 is a double velour fabric for maximizing the advantages of early endotheliazation.

The first fabric spine 78 is desirably folded axially and rolled into the velour fabric 80. The velour fabric 80 is sufficiently greater in lateral dimension that the entire spine fabric 78 is sheathed within the velour fabric 80. The velour fabric 80 is then sutured as at 77 along the forward edge of the prosthesis 70.

The flexible prosthesis 70 thus constructed, can be easily configured in any one of a variety of suitable heart valve configurations including both of those illustrated in FIGS. 2 and 4. The broken line position illustrated in FIG. 9 represents the configuration into which the prosthesis would be configurated upon placement during mitral valve annuloplasty. The length of the prosthesis 70 is specifically constructed such that the ends 72 and 74, when displaced into the proper configuration, will be spaced so as to correspond essentially to the arcuate distance between commissures of the mitral heart valve leaflet. Clearly, the length of the prosthesis 70 may be varied to correspond to any selected heart valve subject to valvular annuloplasty. This flexible prosthesis embodiment has been found highly effective in restoring valve function by constricting the valve annulus without interfering with leaflet mobility.

The invention may be embodied in other specific forms without departing from its spirit or essential characteristics. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope.

What is claimed and desired to be secured by U.S. Letters Patent is:

1. A mitral valve prosthesis comprising in combination:
    an essentially symmetrical, elongated open ring comprising a spine having opposed ends, the ends being spaced one from the other a distance which is selected to permit unencumbered movement of the anterior leaflet of the mitral valve between the ends when the prosthesis is in place in the mitral valve annulus; and
    a double velour fabric sheath substantially encapsulating the spine, the double velour fabric being joined to the spine and extending laterally away from the open ring to form an appendage, both top and bottom of said appendage presenting double velour fabric so as to come into direct contact with surrounding tissue when the prosthesis is in place within the mitral valve annulus.

2. A tricuspid valve prosthesis comprising:
    an asymmetrical, elongated open ring comprising a stiff spine having opposed ends, one of the ends bending through a greater arc than the other end and the ends being spaced one from the other a distance which is selected to permit unencumbered movement of the septal leaflet of the tricuspid valve between the ends when the prosthesis is in place in the tricuspid valve annulus; and
    a double velour fabric sheath substantially encapsulating the spine, the velour fabric being joined to the spine so as to come into direct contact with surrounding tissue when the prosthesis is in place within the tricuspid valve annulus.

3. A heart valve prosthesis comprising a spine portion comprising:
    a flexible fabric, initially straight though bendable into an open ring configuration, the length of the spine portion approximating the arcuate distance between commissures of a selected heart valve leaflet; and
    a velour sheath encapsulating the entire fabric spine portion.

* * * * *